(12) United States Patent
Laing et al.

(10) Patent No.: US 8,061,220 B2
(45) Date of Patent: Nov. 22, 2011

(54) SIMULTANEOUS ASPIRATOR AND DISPENSER FOR MULTIWELL PLATES AND SIMILAR DEVICES

(75) Inventors: Lance G. Laing, Belmont, MA (US); Timothy F. Smith, Dracut, MA (US); John Gerstenmeier, III, Cleveland Heights, OH (US); Gangadhar Jogikalmath, Cambridge, MA (US)

(73) Assignee: SRU Biosystems, Inc., Woburn, MA (US)

( * ) Notice: Subject to any disclaimer, the term of this patent is extended or adjusted under 35 U.S.C. 154(b) by 117 days.

(21) Appl. No.: 12/589,446

(22) Filed: Oct. 23, 2009

(65) Prior Publication Data

US 2010/0043571 A1 Feb. 25, 2010

Related U.S. Application Data

(62) Division of application No. 11/601,020, filed on Nov. 17, 2006, now Pat. No. 7,628,085.

(51) Int. Cl.
*G01N 1/00* (2006.01)
(52) U.S. Cl. .................................. 73/863; 73/863.31
(58) Field of Classification Search ............ 73/863, 73/863.31
See application file for complete search history.

(56) References Cited

U.S. PATENT DOCUMENTS

| | | | |
|---|---|---|---|
| 5,578,270 A | 11/1996 | Reichler et al. | 422/67 |
| 6,096,271 A | 8/2000 | Bogen et al. | 422/64 |
| 6,325,114 B1 | 12/2001 | Bevirt et al. | 141/130 |
| 6,374,683 B1 | 4/2002 | Hunicke-Smith et al. | 73/864.17 |
| 6,537,505 B1 | 3/2003 | LaBudde et al. | 422/103 |
| 6,635,167 B1 | 10/2003 | Batman et al. | 205/775 |
| 6,983,636 B2 | 1/2006 | Johnson et al. | 73/1.36 |
| 2001/0012492 A1 | 8/2001 | Acosta et al. | 422/65 |
| 2002/0127565 A1 | 9/2002 | Cunningham et al. | 435/6 |
| 2003/0027327 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0077660 A1 | 4/2003 | Pien et al. | 435/7.1 |
| 2003/0170145 A1 | 9/2003 | Smith et al. | 422/68.1 |

(Continued)

FOREIGN PATENT DOCUMENTS

JP 2001-523812 11/2001

(Continued)

OTHER PUBLICATIONS

International Preliminary Report on Patentability mailed May 28, 2009 in PCT/US2007/019566, filed Sep. 7, 2007.

(Continued)

*Primary Examiner* — Herzon E Williams
*Assistant Examiner* — Rodney T Frank
(74) *Attorney, Agent, or Firm* — McDonnell Boehnen Hulbert & Berghoff LLP

(57) ABSTRACT

A device for simultaneously dispensing a solution containing a sample to a test device and aspirating the sample from the device. In one embodiment the device is hand-held and includes a control mechanism, e.g., button for activating the dispensing and aspiration of the sample. The testing device may take the form of a multi-well plate with a plurality of wells arranged in rows and columns, with the bottom of the wells formed as a photonic crystal biosensor. The device can be configured with dispense and aspirate manifolds and associated dispense and aspirate ports which are positioned in all the wells along a row or column of wells so as to simultaneously aspirate and dispense solution to all the wells in a row or column of the multi-well plate.

34 Claims, 4 Drawing Sheets

U.S. PATENT DOCUMENTS

2005/0213868 A1    9/2005  Cunningham ............... 385/12

FOREIGN PATENT DOCUMENTS

| | | |
|---|---|---|
| JP | 2006-242858 | 3/2005 |
| JP | 2006-284350 | 3/2005 |
| WO | WO 99/025476 | 5/1999 |

OTHER PUBLICATIONS

International Search Report and Written Opinion in PCT/US2007/019566, dated Jan. 18, 2008.

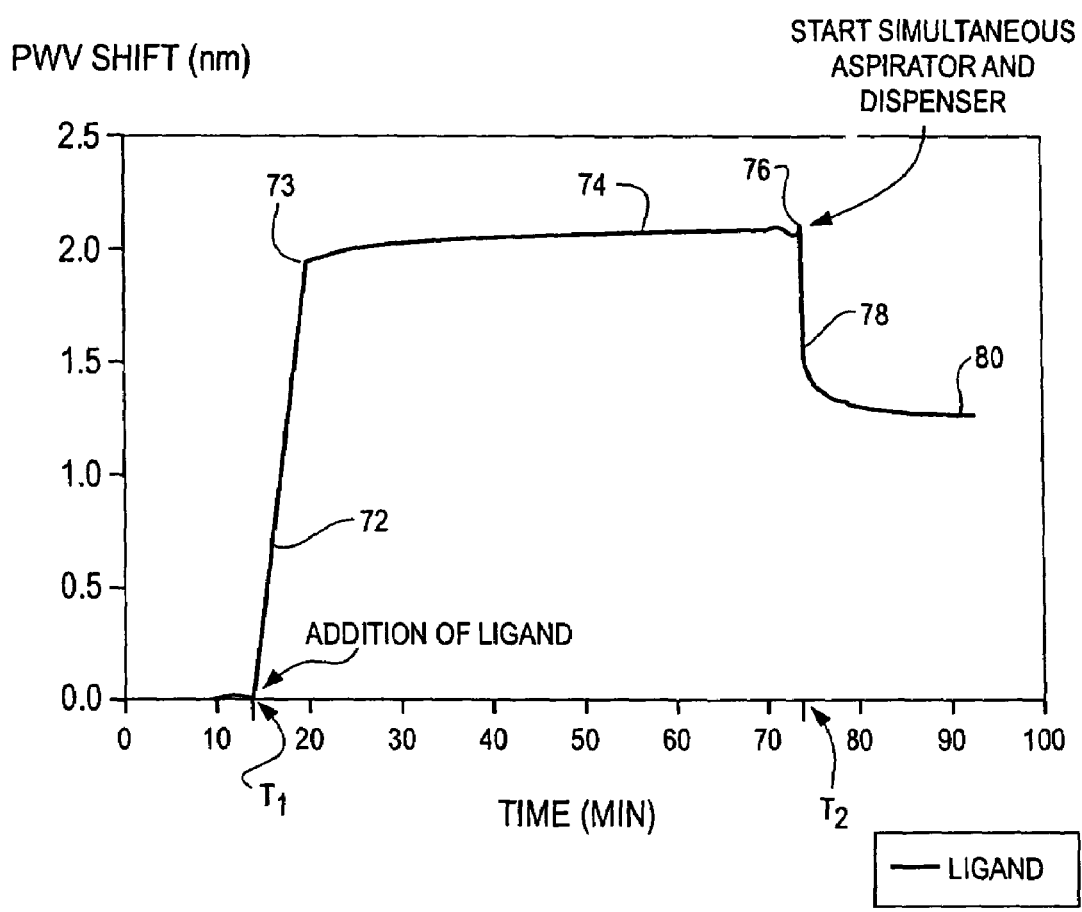

SIMULTANEOUS ASPIRATOR AND DISPENSER FOR MULTIWELL PLATES AND SIMILAR DEVICES

CROSS-REFERENCE TO RELATED APPLICATION

This is a divisional of U.S. application Ser. No. 11/601,020 filed Nov. 17, 2006, now allowed, the content of which is incorporated by reference herein.

BACKGROUND

This disclosure relates to the art of devices used for aspirating and dispensing small quantities of fluids. More particularly, the disclosure relates to a combination aspirating and dispensing device suitable for use with test devices having a sample containment region in the form of one or more wells or columns of wells, for example in the form of a multi-well plate.

Test devices in the field of biology and biochemistry can take a variety of forms, including devices arranged in an array of wells, such as an 8×12 array of wells arranged in rows and columns. In order to conduct a test on the sample the sample must be loaded into the well. A variety of dispensing devices are known in the art, and described in the patent literature. See, for example, U.S. Pat. Nos. 5,578,270; 6,374,683; 6,325,114; 6,537,505 and 6,983,636. Some of these dispensing devices are automated, while others require a human operator to manually dispense a sample into a well of a test device.

The assignee of this invention has developed a grating-based biosensor which can be affixed to the bottom of a bottom-less multiwell plate whereby the multiwell plate forms a receptacle for holding a biochemical sample to be tested. Grating-based sensors represent a new class of optical devices that have been enabled by recent advances in semiconductor fabrication tools with the ability to accurately deposit and etch materials with precision less than 100 nm.

Several properties of photonic crystals make them ideal candidates for application as grating-type optical biosensors. First, the reflectance/transmittance behavior of a photonic crystal can be readily manipulated by the adsorption of biological material such as proteins, DNA, cells, virus particles, and bacteria on the crystal. Other types of biological entities which can be detected include small and smaller molecular weight molecules (i.e., substances of molecular weight <1000 Daltons (Da) and between 1000 Da to 10,000 Da), amino acids, nucleic acids, lipids, carbohydrates, nucleic acid polymers, viral particles, viral components and cellular components such as but not limited to vesicles, mitochondria, membranes, structural features, periplasm, or any extracts thereof. These types of materials have demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding on the surface of the grating while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3-5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of grating-type biosensors in the prior art are disclosed in Cunningham, B. T., P. Li, B. Lin, and J. Pepper, *Colorimetric resonant reflection as a direct biochemical assay technique*. Sensors and Actuators B, 2002. 81: p. 316-328; Cunningham, B. T., J. Qiu, P. Li, J. Pepper, and B. Hugh, *A plastic calorimetric resonant optical biosensor for multiparallel detection of label-free biochemical interactions*, Sensors and Actuators B, 2002. 85: p. 219-226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles*. Journal of the American Chemical Society, 2002. 124: p. 10596-10604.

The photonic crystal biosensors of the assignee and associated detection instruments for label-free binding detection are also described in the patent literature; see U.S. patent application publications U.S. 2003/0027327; 2002/0127565, 2003/0059855 and 2003/0032039. Methods for detection of a shift in the resonant peak wavelength are taught in U.S. Patent application publication 2003/0077660. The above-references patent applications and articles are hereby incorporated by reference in their entirety.

There is currently a need in the art for simple, easy to use device which allows for simultaneous dispensing and aspirating of a solution containing a test sample onto a testing device, e.g., one configured in an array of wells. This invention meets that need.

SUMMARY OF THE INVENTION

The following embodiments and aspects thereof are described and illustrated in conjunction with systems, tools and methods which are meant to be exemplary and illustrative, not limiting in scope. In various embodiments one or more of the above-described problems have been reduced or eliminated, while other embodiments are directed to other improvements.

In a first aspect, a device is disclosed which provides for simultaneously dispensing and aspirating a sample to a testing device. The testing device can take a variety of forms. The embodiments will be described below in conjunction with a testing device in the form of a multi-well plate having a plurality of sample wells arranged in rows and columns. The principles of operation of the device are applicable to other types of testing devices.

The dispensing and aspirating device includes a body having a portion thereof, such as the bottom surface of the body, adapted for engagement with the testing device. In the context of the multi-well test device, the bottom surface of the body rests on the top surface of the multi-well testing device when the dispensing and aspirating device is in use. The device further includes dispense tubing coupled to the body for receiving a sample (e.g., fluid solution containing a sample) from a source. The device further includes aspirate tubing coupled to the body which is connected to a source of vacuum. The device further includes a dispense manifold connected to the dispense tubing having at least one dispensing port and an aspirate manifold connected to the aspirate tubing having at least one aspirating port.

The dispensing and aspirating device further includes a control mechanism, e.g., in the form of one or more valves and button or switch for operating the valves, for controlling movement of the sample from the dispense tubing to the dispense port and for simultaneously controlling the application of vacuum in the aspirate tubing-to the aspirating port. When the control mechanism is operated (e.g., by pressing on a button and responsively opening the valves), fluid solution containing the sample is introduced into the dispense manifold and exits the dispensing port whereby the sample is introduced into the test device. Simultaneously, the vacuum is applied to the aspirating port in the aspirate manifold and the sample which is applied. to the test device can be withdrawn.

As noted, the testing device may take the form of a multi-well testing device arranged in one or more rows of a plurality of wells. The dispense and aspirate device is configured such that the dispense and aspirate manifolds include a dispensing and aspirating port for each well in the row of wells in the multi-well test device. Accordingly, when the control mechanism is activated, sample is introduced into each well in the row of wells and the sample solution is also aspirated from each of the wells in the row of wells.

The aspirating and dispensing device is particularly well suited for testing devices that are configured in the form of a grating-based biosensor. The aspirating and dispensing device can be used to dispense and aspirate a sample onto the biosensor surface while the detection instrument for the biosensor simultaneously operates to generate optical measurements from the testing device, such as the shift in peak wavelength value due to binding of the sample to the surface of the biosensor.

In another aspect, a method is disclosed for simultaneously dispensing and aspirating a sample to a testing device having at least one well. The method comprises the steps of: positioning an aspirating and dispensing device over the testing device such that an aspirating port and a dispensing port in the device are placed into the at least one well, and activating a control mechanism to thereby cause a sample to enter the well via the dispensing port and simultaneously aspirating the sample from the well. In one embodiment, the testing device takes the form of a multi-well device having a plurality of wells arranged in one or more rows of wells. During the positioning step an aspirating port and a dispensing port are placed into all the wells in one of the rows of wells of the multi-well device.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 4 shows the PWV shifts for three different rates of sample dispensing and aspirating.

FIG. 8 is a graph of shift in peak wavelength value (PWV) as a function of time for a sample placed in a well of biosensor used with the device of FIGS. 1-3 or 5-7, showing the acquisition of on- and off-rate data indicating rates at which binding events occur in the biosensor wells, with the off-rate data acquired using simultaneous aspirating and dispensing features of the apparatus of FIGS. 1-3 or FIGS. 5-7.

DETAILED DESCRIPTION

Figure 1:
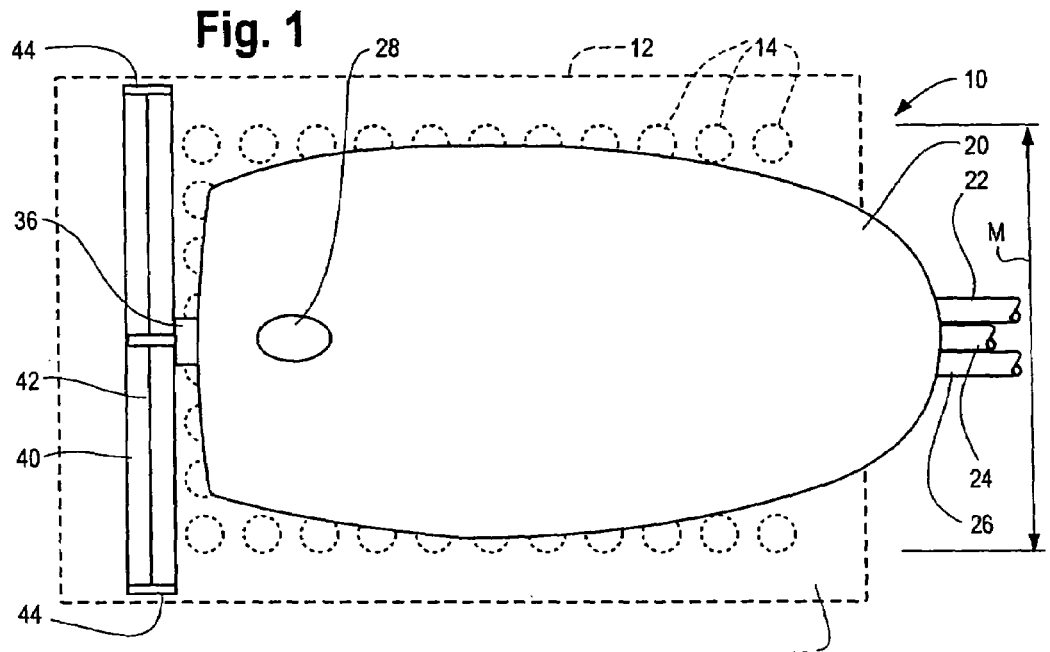
FIG. 1 is a plan view of an embodiment of the dispensing and aspirating device showing the device resting on the top surface of a testing device in the form of a multi-well microtiter plate, with an aspirating port and a dispensing port positioned in each of the wells in a row of wells in the multi-well plate for simultaneous dispensing and aspirating of a sample into each sample well in a row of the wells.
Figure 2:
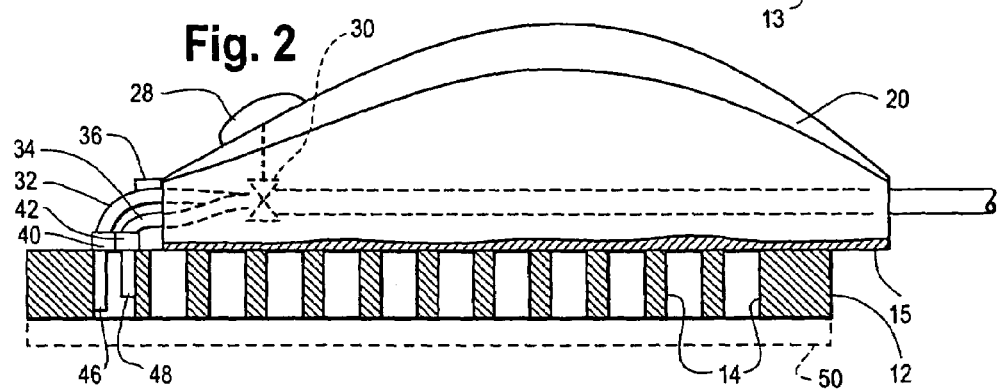
FIG. 2 is a cross-sectional view of the device of FIG. 1, taken along the lines 2-2 of FIG. 1.
Figure 3:
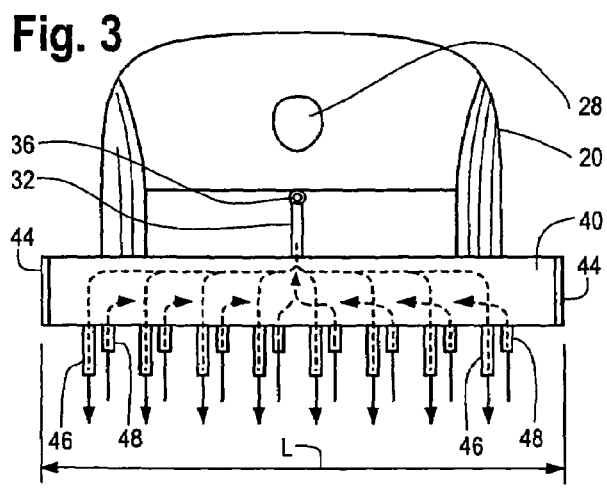
FIG. 3 is an end view of the device of FIGS. 1 and 2, shown isolated from the testing device. The height of the dispense manifold and the dispense and aspiration ports are shown somewhat exaggerated in FIG. 3 in order to show the structure of the device.

FIG. 1 is a plan view of an embodiment of a dispensing and aspirating device 10 showing the device 10 resting on the top surface 13 of a testing device 12 in the form of microtiter plate having wells 14 arranged in a plurality of rows and columns. FIG. 2 shows the device 10 in cross-section along the lines 2-2 of FIG. 1. FIG. 3 is an end view of the device 10 shown isolated from the testing device 12.

The dispensing and aspirating device 10 includes a body or enclosure 20 which has bottom surface portion 15 which is given a substantially planar configuration (best shown in FIGS. 2 and 3) so that the enclosure 20 may rest upon and thereby engage the top surface 13 of the testing device 12 during use. The device 10 includes dispense supply tubing 22 which is coupled to the body 20. The dispense supply tubing 22 carries a fluid solution containing sample from a source (not shown) and delivers the solution to the enclosure 20. The enclosure includes additional conduits (shown in dashed lines in FIG. 2) and a dispense inlet tube 32 for carrying the sample to a dispense manifold 40. A valve 30. (FIG. 2) or other flow regulation device is placed within the enclosure 20 to regulate the flow of the sample solution, to the dispense manifold 40.

Dispense return tubing 24 is also coupled to the body 20. The dispense return tubing 24 allows for a continuous loop of the dispensing solution through the device and back to the solution reservoir connected to the supply tubing 22 at a constant flow rate and pressure until the valve 30 is opened and the solution is able to travel into the wells 14. This loop consisting of supply tubing 22 and return tubing 24 allows for a pump to be attached to the device and connected to the tubing and thus providing the constant flow and pressure. If there was no loop, the flow rate would accelerate from 0 to a set value as the solution is allowed to enter the wells. The pressure would also decrease after being allowed by the valve to enter the wells.

The body 20 is also coupled to aspirate tubing 26 which is connected to a source of vacuum. The aspirate tubing 26 is connected to internal conduits which supply the vacuum to an aspirate manifold 42. A valve or like device is placed within the body 20 to regulate the application of vacuum to the aspirate manifold 42.

The dispense manifold 40 includes at least one dispensing port 46. In the embodiment of FIGS. 1-3, there are eight dispensing ports 46 connected to the dispense manifold, one for each well in a row of wells in the testing device 12.

Similarly, the aspirate manifold 42 includes at least one aspirating port 48. In the embodiment of FIGS. 1-3, there are eight aspirating ports 48 connected to the aspirate manifold 42, one for each well in a row of wells. The aspirate outlet 34 couples the aspirate manifold 42 to the valve 30 connected to the aspirate tubing 26.

As will be appreciated from FIGS. 2 and 3, the ports 46 and 48 are positioned in close proximity to each other and grouped in pairs, such that one dispensing port and one aspirating port are positioned within each well across the row of wells 14.

The aspirate and dispense manifolds 40 and 42 include removable end caps 44 which allow for cleaning and disinfection of the interior of the manifolds 40 and 42 after use.

The device 10 further includes a control mechanism for controlling movement of the sample from the dispense tubing 22 to the dispense ports 46 and for simultaneously controlling application of vacuum in the aspirate tubing 26 to the aspirating ports 48. In one embodiment shown in FIGS. 1-3, the control mechanism takes the form of a manually actuated button 28 positioned on the top surface of the enclosure or body 20. When the button 28 is depressed, a valve 30 (FIG. 2) in the enclosure 20 is opened to cause solution (under positive pressure) in the dispense supply tubing 22 to enter and fill the dispense manifold 40 and exit the dispense ports 46 into each of the wells of a row of wells in the microtiter plate 12. Simultaneously, a second valve 30 is opened allowing vacuum present in the aspirate tubing 26 to be applied to the aspirate manifold 42. The vacuum is present at the tip of the aspirate ports 48, which then withdraws the solution from the wells. Consequently, by virtue of the design shown in FIGS. 1-3, with an aspirating port and a dispensing port positioned in each of the wells in a row of wells in the multi-well testing device 12, when the control mechanism or button 28 is depressed, the device 10 simultaneously dispenses a sample into each sample well in a row of the wells and aspirates the sample from the each well.

While the are eight aspirating ports and eight dispensing ports in the embodiment of FIGS. 1-3, arranged in pairs as shown in FIG. 3, the number of ports can of course be increased or decreased as necessary to accommodate testing devices with different numbers of wells in a row of wells.

In order to dispense and aspirate solution containing a sample to all the wells in the row simultaneously, the aspirate and dispense manifolds 40 and 42 are given an elongate tubular channel configuration shown in FIG. 3 having a length L. Additionally, the testing device 12 consists of an array of wells 14 arranged in rows and columns, and wherein at least one of the rows and columns of wells is of a linear dimension M (see FIG. 1), and where $L \geq M$. Additionally, there is one aspirating port 48 and one dispensing port 46 in a spaced relation along the length of the aspirate and dispense manifolds 42 and 40 for each well 14 in the rows of wells of length M, as shown in FIGS. 1-3.

In the embodiment of FIGS. 1-3, the body 20 is sized and shaped so as to be held in a human hand, e.g., the body can be shaped similar to a computer mouse. The manually-activated control device 28 is incorporated into the body 20, e.g., on the top of the body 20 where it can be depressed by the index finger. The user operates the control device 28 to dispense and aspirate solution into all the wells in one row simultaneously, then lifts the device 10 from the testing device 12 and positions the ports 46 and 48 into the wells of the next row of wells, activates the control mechanism or button 28, and then repeats the process for the remaining rows of wells. It will be noted from FIGS. 2 that the tips of the dispensing and aspirating ports 46 and 48 extend into wells 14 formed in the top surface 13 of the testing device 12 when the lower surface 15 of the body 20 is engaged with the top surface 13 of the testing device.

In the embodiment of FIGS. 1-3, the device 10 further includes an auxiliary injection port 36 for receiving a second sample for introduction to the testing device 12.

Figure 4:
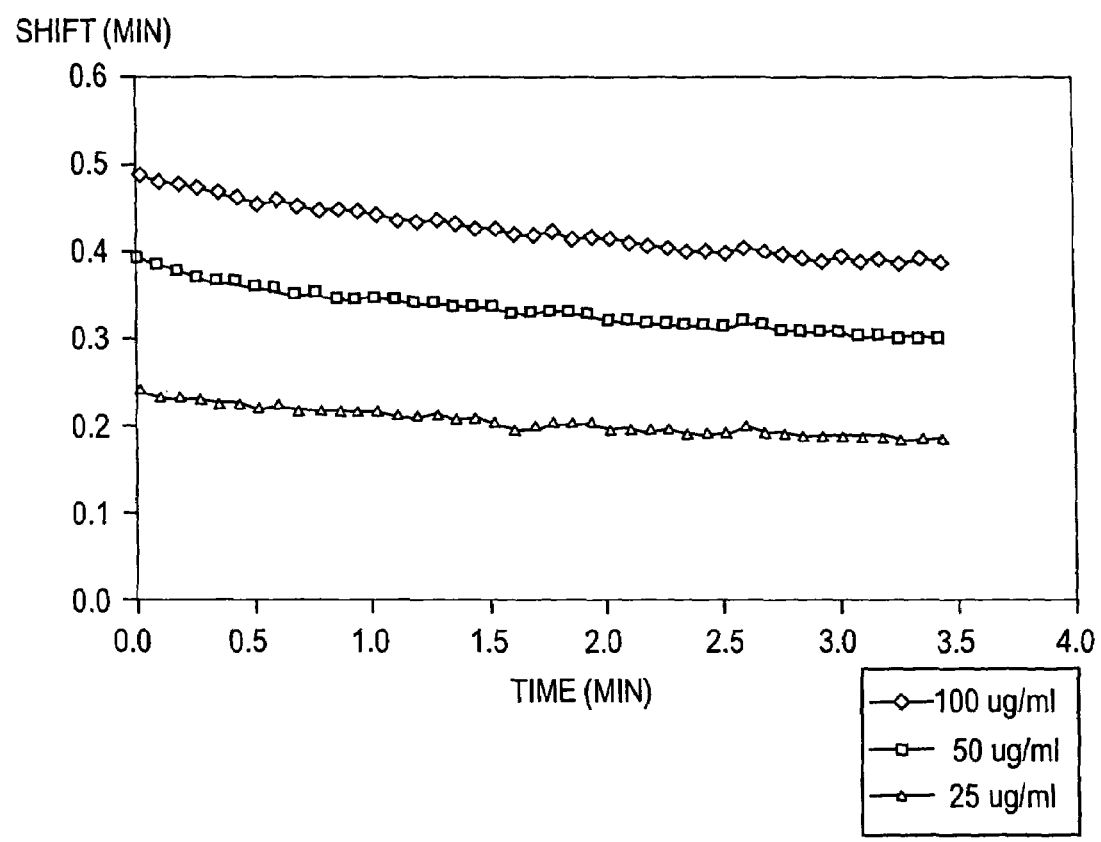
FIG. 4 is a graph of shift in peak wavelength value (PWV) (in nm) as a function of time for a sample simultaneously dispensed into and aspirated from a well of the test device of FIGS. 1-3.

The device 10 of FIGS. 1-3 is particularly well suited for use in conjunction with testing devices 12 which include plurality of wells for receiving the sample, and in which the wells have a bottom surface for receiving the sample constructed as a grating-based biosensor 50 (FIG. 2). See the references disclosed in the Background section as examples of such grating-based biosensors. One virtue of the present dispensing and aspirating device 10 is that that the device may be operated to dispense and aspirate solution containing a biochemical sample to the testing device while the testing device is being read by optical detection instrumentation. Accordingly, the testing device 12 can be used to detect binding interactions on the surface of the biosensor 50 (e.g., shifts in PWV), at different rates for dispensing and aspiration. For example, FIG. 4 is a graph of shift in peak wavelength value (PWV) (in nm) as a function of time for a sample introduced into a well of the test device of FIGS. 1-3 that is configured as a grating-based biosensor. FIG. 4 shows the PWV shifts for three different rates of sample dispensing and simultaneous aspiration.

As noted above, the control mechanism 28 in one embodiment is manually operated, by the user of the device manually depressing the dispensing button 28 to thereby open the valves and allow the dispensing and aspirating to occur. The dispensing and aspirating continues as long as the button 28 is held down.

Figure 5:
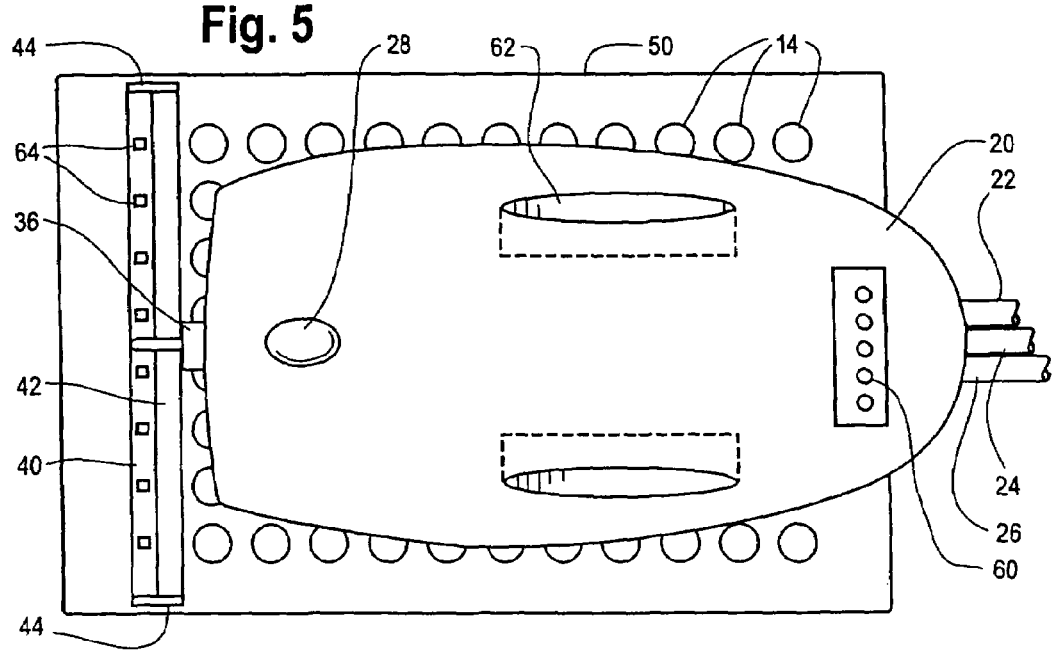
FIGS. 5-7 are plan, end and side views, respectively, of an alternative embodiment of the aspirating and dispensing device of FIGS. 1-3, which may include one or more features including a gripping feature by which the device may be gripped by a robotic arm, sensors for sending chemical properties in the well such as pH or temperature, microfluidic valves, and an electrical connector for coupling the device to an electronics unit for control by a robot, variable flow pump control, sensor signal output, and/or valve control.
Figure 6:
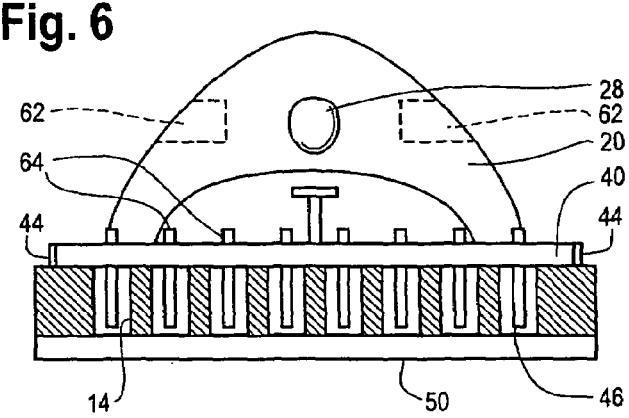
Figure 7:
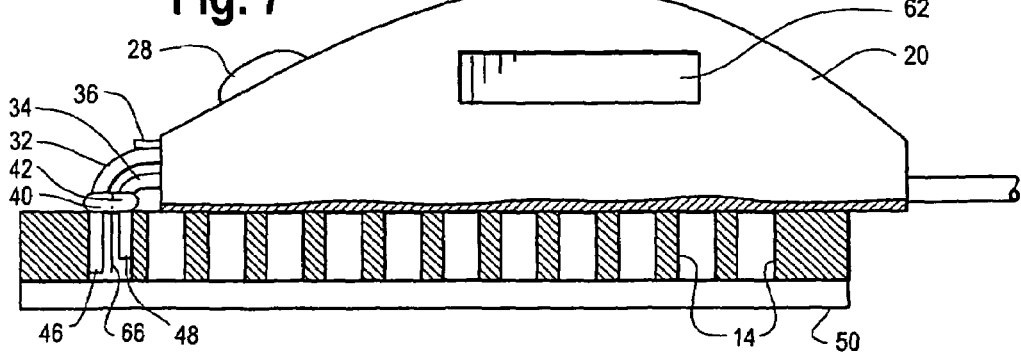

In one possible variation, the entire dispensing and aspirating device 10 could be designed for an automated system automatically dispensing and aspirating solution containing a sample into a testing device, in which situation the control mechanism 28 could by automatically operated. FIGS. 5-7 show an alternative configuration designed for automatic operation, e.g., with movement by a robotic and control via electronic controls. In this embodiment, the body 20 includes a pair of robot gripping features, e.g., slots 62 formed in the side of the body by which a robotic hand or arm may grip the device, lift it up and place it down, so that the probes are sequentially placed in rows of wells in the test device. The particular type of gripping feature in the body 20 is not particularly critical and can be adapted to the particular hand or arm construction of the robot being used with the device. The body 20 further includes an electrical connector 60 with a set of pins for connection to wires leading to electronic controls for the valve(s) 30 (FIG. 2) in the body. In this case, the valve(s) are electrically operated and open and close in response to signals supplied to the body via the electrical connector 30. The electrical connector will also include pins for variable flow pump control, and output of signals from pH, temperature, or other sensors 66.

In this embodiment, the device 10 could be attached to a robotic arm (not shown) which lifts the device 10 into and out of engagement with the top surface. of the testing device 12. The operation of the dispensing and aspirating mechanisms could be performed by switching on and off electrically-operated valves which are either built into the device 10 or which are otherwise in the fluid path between the source of solution and the dispensing ports and between the source of vacuum and the aspirating ports. Persons skilled in the art can readily adapt the disclosed embodiment to an automated dispensing and aspirating embodiment without undue difficulty, given the state of the art of robotics and electronic control systems.

In another variation of the embodiment of FIGS. 1-3, an electronic control mechanism from the aspirating and dispensing device may operate a variable flow pump that directs sample to the testing device 12, either in addition to a valve 30 or in lieu of the valve 30. The variable flow pump could be positioned upstream of the device 10, but operated by actuation of a button or other manual control incorporated into the device 10. For example, the device 10 could include a dial, thumb wheel, or other type of manual control which adjusts the setting of the variable flow pump. Such control feature may also include a dial to display to the operator the current setting of the variable flow pump.

In another possible variation, the device 10 can further include one or more sensors 66 (FIG. 7) for making a measurement of a sample delivered by the aspirating and dispensing device to the wells 14 of the testing device. For example, a sensor 66 such as a temperature sensor, pH sensor, or an ionic strength sensor could be incorporated into the device and positioned or mounted adjacent to at least one of the aspirating port 46 or the dispensing port 48, as shown in FIG. 7. More than one type of sensor could be incorporated. Furthermore, the sensor(s) could be provided for each pair of dispensing and aspirating ports, or just for one pair of dispensing and aspirating ports. The output of the sensors is supplied to the control electronics (not shown) via the connector 60 of FIG. 5. For example, the sensors 66 can be coupled to a processing unit (not shown) that controls delivery of the sample to the testing device 12 using a feedback loop incorporating sensor data reported by the at least one sensor. For example, if the device includes a pH sensor, the processing unit adjusts the pressure in the dispense supply tubing 22 according to the pH reading provided by the pH sensor.

In still another variation, the aspirating and dispensing device 10 may further be associated with a temperature controller (not shown) which controls the temperature of the sample delivered to the testing device 12. The temperature controller may include a temperature sensor (either the sensor 66 in the well 14 or in the body 20 or elsewhere) and a heating element or cooling element to heat or cool the sample as needed so that the sample is introduced to the wells of the testing device 12 at a desire temperature or in accordance with a desired temperature profile.

As shown in FIGS. 5-7, the aspirating and dispensing device further includes eight microfluidic valves 64 which are placed in the dispense manifold 40 and control dispensing of sample into the eight wells in a row of wells 14 in the test device 12. The microfluidic valves 64 can be either mechanically or electrically operated, e.g., in response to depression of the button 28 or by signals supplied to the device via the connector 60.

In view of the above, it will also be appreciated that we have disclosed a method of simultaneously dispensing and aspirating a sample to a testing device 12 having at least one well 14, comprising the steps of: positioning an aspirating and dispensing device 10 over the testing device 12 such that an aspirating port 48 and a dispensing port 46 in the device 10 are placed into the at least one well 14; and activating a control mechanism (28) to thereby cause a sample to enter the well 14 via the dispensing port 46 and simultaneously aspirating the sample from the well via the aspirating port 48. In one configuration, as shown in FIGS. 1 and 2, the testing device 12 comprises a multi-well device (e.g., 96 well microtiter plate) having a plurality of wells 14 arranged in rows and columns, and wherein during the positioning step an aspirating port 48 and a dispensing port 46 are placed into all the wells in a row or column of wells of the multi-well device 12.

As noted above, the activating step can be performed manually. It can also be performed automatically, e.g., in an automated implementation of the device 10.

As noted further, the method may further involve making measurements of the sample with a sensor. The sensor may for example take the form of a temperature sensor, a pH sensor, or an ionic strength sensor. All three sensors may be incorporated into the device.

In one configuration, the sensor is a temperature sensor and the method further includes the step of controlling the temperature of the sample delivered to the testing device 12.

In one possible use of the device 10, the aspirating and dispensing steps may be performed simultaneously with optical measurements taken of the testing device, e.g., measurements of shift in PWV indicating binding events occurring on the surface of the testing device. For example, FIG. 4 shows a graph of shift of PWV of a Mouse IgG sample as a function of time at three different sample dispensing rates. The data is captured by an imaging instrument as disclosed in the above-references SRU Biosystems, Inc. published U.S. patent application documents.

Measurements of Equilibrium Dissociation and Association Constants Using Device 10

The device 10 of FIGS. 1-3 and 5-7 can be used to measuring equilibrium dissociation and association constants of a sample being tested. One traditional biochemical definition of affinity between two molecules involves the measurement of the equilibrium dissociation constant or the equilibrium association constant. These can be defined by the following equations:

$$K_d = k_{off}/k_{on} \text{ and} \qquad 1)$$

$$K_a = k_{on}/k_{off} \text{ where} \qquad 2)$$

$K_d$ is the equilibrium dissociation constant;
$K_a$ is the equilibrium association constant;
$k_{off}$ is the rate that the two molecules come apart;
$k_{on}$ is the rate that the two molecules bind together.

The device 10 of this disclosure is suitable for measurement of the constants $K_a$ and $K_d$. In particular, the device 10 allows one to acquire off-rate data on a multi-well plate biosensor without having to manually aspirate and dispense a solution with a handheld multi-channel pipettor. The device 10 allows for a constant simultaneous flow of solution into and out of the wells while data acquisition is occurring. This is not feasible with a hand-held pipettor since the flow rates are not capable of precise control with hand-operated instruments such as a pipettor. However, precise flow rates are possible with the aspirating and dispensing device 10 of this disclosure.

The steps to make the on- and off- rate measurements and determination of constants $K_a$ and $K_d$ will now be explained in conjunction with FIGS. 1 and 8. A sample holder is used in the form of a multi-well plate 12 with the bottom of the wells 14 of the plate 12 formed as a photonic crystal biosensor 50 as described above and in the patent applications of the assignee SRU Biosystems cited previously in this document. A buffer solution is added to one of the wells of the biosensor. The biosensor is placed onto an detection instrument for detecting the peak wavelength value of light reflected from the surface of the biosensor as described in the above-cited SRU published patent application documents. A baseline PWV of buffer is measured by the detection instrument. See FIG. 8, curve between time 10 minutes and time T1. Next, a ligand is then added to the well of the biosensor and mixed with the buffer. This occurs at time T1 in FIG. 8.

The detection instrument continues to make measurements of the shift in the PWV as the sample is added. There is an increase in the PWV signal, as indicated in FIG. 8 at 72. The on-rate ($k_{on}$) is the measurement of the change in Shift vs the change in Time, i.e., the slope of the curve of FIG. 8 at region 72.

After a period of time the ligand comes to equilibrium and the PWV shift plateaus. See FIG. 8, point 73 and region 74.

At time T2, the Simultaneous Aspirator and Dispenser 10 (FIG. 1) is then placed on the sensor with a pair of the aspiration and dispenser probes placed into the well containing the buffer+ligand. The valve 30 in the dispenser 10 is opened in order to start the flow of buffer into the wells via the dispense probe 46 (FIG. 2). Aspiration of buffer via the aspiration probe 48 (FIG. 2) is also activated in order to keep the buffer at a steady flow over the sensor, with the rate of aspiration equal to the rate of dispensing.

As indicated at FIG. 8 at 76 and 78, the detection instrument records a decrease in PWV signal, as there is now a new equilibrium state for the ligand with a change in the buffer in the well. This negative change in PWV Shift as a function of time is the off-rate ($k_{off}$), i.e., the slope of the curve at point 78. Eventually the shift in PWV plateaus as indicated at 80.

From the measurements of $k_{on}$ and $k_{off}$ one can compute the equilibrium disassociation and association constants using equations 1) and 2).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

We claim:

1. A device for simultaneously dispensing and aspirating a sample to a testing device having a well, comprising:
   a) a body having a portion thereof adapted for engagement with the testing device;
   b) dispense tubing coupled to the body for receiving a sample from a source;
   c) aspirate tubing coupled to the body connected to a source of vacuum;
   d) a dispense manifold connected to the dispense tubing having at least one dispensing port;
   e) an aspirate manifold connected to the aspirate tubing having at least one aspirating port wherein the dispensing port and the aspirating port are configured in close proximity to each other whereby the aspirating port and dispensing port are positioned in or proximate to the well of the testing device when the body is positioned proximate to the testing device; and
   f) a control mechanism for controlling movement of the sample from the dispense tubing to the dispense port and for simultaneously controlling application of vacuum in the aspirate tubing to the aspirating port to thereby permit simultaneous dispensing a sample to the well and aspirating the sample from the well.

2. The device of claim 1, wherein testing device comprises a multi-well testing device arranged in one or more rows of a plurality of wells, and wherein the dispense and aspirate manifolds include a dispensing and aspirating port for each well in the row of wells in the multi-well test device.

3. The device of claim 1, wherein the body is sized and shaped so as to be held in a human hand and wherein the control mechanism includes a manually-activated control device incorporated into the body.

4. The device of claim 3, wherein the control device activates a valve coupling the dispense tubing to the dispensing manifold and a valve coupling the aspirate tubing to the aspirate manifold.

5. The device of claim 1, wherein the device further comprises an auxiliary injection port for receiving a second sample for introduction to the testing device.

6. The device of claim 1, wherein the testing device includes a plurality of wells for receiving the sample and wherein the wells have a bottom surface for receiving the sample constructed as a grating-based biosensor.

7. The device of claim 6, wherein the body further comprises a lower surface for engaging a top surface of the testing device, and wherein the testing device further comprises a plurality of wells, and wherein the dispensing and aspirating ports further comprise tips thereof which extend into wells formed in the top surface of the testing device when the lower surface of the body is engaged with the top surface of the testing device.

8. The device of claim 1, wherein the control mechanism is manually operated.

9. The device of claim 1, wherein the control mechanism is automatically operated.

10. The device of claim 1, wherein the device comprises at least eight aspirating ports and at least eight dispensing ports.

11. The device of claim 10, wherein the aspirating and dispensing ports are spatially arranged in at least eight pairs of aspirating and dispensing ports.

12. The device of claim 1, further comprising a variable flow pump for directing sample to the testing device via the dispense tubing.

13. The device of claim 1, wherein the device further comprises at least one sensor for measurement of a sample delivered by the device to the testing device.

14. The device of claim 13, wherein the sensor is selected from the group of sensors consisting of a) a temperature sensor, b) a pH sensor, and c) an ionic strength sensor.

15. The device of claim 13, wherein the at least one sensor is mounted adjacent to at least one of the aspirating port or the dispensing port.

16. The device of claim 13, further comprising a processing unit controlling delivery of the sample to the testing device using a feedback loop incorporating sensor data reported by the at least one sensor.

17. The device of claim 1, wherein the device further comprises a temperature controller controlling the temperature of the sample delivered to the testing device.

18. The device of claim 1, wherein the aspirate and dispense manifolds comprise elongate tubular channels having a length L, wherein the testing device comprises an array of wells arranged in rows and columns, and wherein at least one of the rows and columns of wells is of a linear dimension M, where $L \geq M$, and wherein there is one aspirating port and one dispensing port in a spaced relation along the length of the aspirate and dispense manifolds for each well in the rows or columns of wells of length M.

19. The device of claim 1, wherein the sample comprises a buffer.

20. Apparatus for simultaneously dispensing and aspirating a sample to a testing device having a well, comprising:
   a dispensing and aspirating device having a dispensing port in fluid connection with a source of a sample and an aspirating port;
   wherein the dispensing port and the aspirating port are configured in close proximity to each other whereby the aspirating port and dispensing port are positioned in or proximate to the well of the testing device when the dispensing and aspirating device body is positioned proximate to the testing device; and a control mechanism controlling movement of the sample through the dispensing and aspirating device enabling the sample to be simultaneously dispensed into the well via the dispense port and simultaneously aspirated the sample from the well via the aspirating port.

21. The apparatus of claim 20, wherein the testing device comprises a multi-well plate and a plurality of wells arranged in rows and columns, and wherein the dispensing and aspirating device comprises a plurality of pairs of aspirating ports and dispensing ports adapted and spaced from each other so that a sample can be simultaneously aspirated and dispensed into each well in a row or column of wells in the multi-well plate.

22. The apparatus of claim 20, wherein the sample comprises a buffer.

23. The apparatus of claim 20, where in the dispensing and aspirating device includes body sized and shaped so as to be held in a human hand and wherein the control mechanism includes a manually-activated control device incorporated into the body.

24. The apparatus of claim 23, wherein the body further comprises a lower surface for engaging a top surface of the testing device, and wherein the dispensing and aspirating ports further comprise tips thereof which extend into the well when the lower surface of the body is engaged with the top surface of the testing device.

25. The apparatus of claim 20, wherein the dispensing and aspirating device further comprises an auxiliary injection port proximate to the dispensing port and the aspirating port for introduction of a second sample into the well of the testing device.

26. The apparatus of claim 20, wherein the testing device includes a plurality of wells for receiving the sample and wherein the wells have a bottom surface for receiving the sample constructed as a grating-based biosensor.

27. The apparatus of claim 20, wherein the control mechanism is manually operated.

28. The apparatus of claim 20, wherein the control mechanism is automatically operated.

29. The apparatus of claim 20, wherein the aspirating and dispensing device comprises at least eight aspirating ports and at least eight dispensing ports, spatially arranged in at least eight pairs of aspirating and dispensing ports.

30. The apparatus of claim 20, wherein the aspirating and dispensing device further comprises at least one sensor for measurement of the sample.

31. The apparatus of claim 30, wherein the sensor is selected from the group of sensors consisting of a) a temperature sensor, b) a pH sensor, and c) an ionic strength sensor.

32. The apparatus of claim 30, wherein the at least one sensor is mounted adjacent to at least one of the aspirating port or the dispensing port.

33. The apparatus of claim 30, further comprising a processing unit controlling delivery of the sample to the testing device using a feedback loop incorporating sensor data reported by the at least one sensor.

34. The apparatus of claim 20, wherein the aspirating and dispensing device further comprises a temperature controller controlling the temperature of the sample delivered to the testing device.

* * * * *